US009546995B2

(12) United States Patent
Jeon et al.

(10) Patent No.: US 9,546,995 B2
(45) Date of Patent: Jan. 17, 2017

(54) NANOPORE DEVICE INCLUDING GRAPHENE NANOPORE AND METHOD OF MANUFACTURING THE SAME

(71) Applicant: Samsung Electronics Co., Ltd., Suwon-si, Gyeonggi-do (KR)

(72) Inventors: Tae-han Jeon, Hwaseong-si (KR); Jeo-young Shim, Yongin-si (KR); Kun-sun Eom, Seoul (KR); Dong-ho Lee, Seongnam-si (KR); Joo-ho Lee, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 11 days.

(21) Appl. No.: 14/257,654

(22) Filed: Apr. 21, 2014

(65) Prior Publication Data
US 2015/0069329 A1 Mar. 12, 2015

(30) Foreign Application Priority Data

Sep. 12, 2013 (KR) ........................ 10-2013-0109974

(51) Int. Cl.
*G01N 27/327* (2006.01)
*G01N 27/453* (2006.01)
*G01N 27/447* (2006.01)
*H01L 29/66* (2006.01)
*H01L 21/768* (2006.01)
*H01L 29/16* (2006.01)
(Continued)

(52) U.S. Cl.
CPC ..... *G01N 33/48721* (2013.01); *B81C 1/00087* (2013.01)

(58) Field of Classification Search
CPC ........................ G01N 27/3278; G01N 27/4146
USPC ........ 257/29, 76, E29.166; 438/42, 149, 198
See application file for complete search history.

(56) References Cited

U.S. PATENT DOCUMENTS

| 8,361,853 B2 | 1/2013 | Cohen et al. |
| 2005/0130387 A1* | 6/2005 | Hakey ............... H01L 21/76283 438/424 |

(Continued)

FOREIGN PATENT DOCUMENTS

| KR | 2012-0136118 A | 12/2012 |
| KR | 2012-0137053 A | 12/2012 |
| WO | 2011/046706 A1 | 4/2011 |

OTHER PUBLICATIONS

Eom et al., DNA-Gated Graphene Nanopore FETs, *Research Paper—Bio Research Center and Device Research Center, Samsung Advanced Institute of Technology* pp. 1-29 (2013).
(Continued)

*Primary Examiner* — Kimberly Rizkallah
*Assistant Examiner* — Brian Turner
(74) *Attorney, Agent, or Firm* — Leydig, Voit & Mayer, Ltd.

(57) ABSTRACT

Provided are a nanopore device with resolution improved by graphene nanopores, and a method of manufacturing the same. The nanopore device includes: a first insulating layer; a graphene layer disposed on the first insulating layer and having a nanopore formed at a center portion of the graphene layer; and first and second electrode layers disposed respectively at both sides of the nanopore on a top surface of the graphene layer, wherein a center region of the first insulating layer is removed such that the center portion of the graphene layer is exposed to the outside.

12 Claims, 7 Drawing Sheets

(51) Int. Cl.
  *G01N 33/487* (2006.01)
  *B81C 1/00* (2006.01)

(56) References Cited

U.S. PATENT DOCUMENTS

| | | |
|---|---|---|
| 2010/0327847 A1 | 12/2010 | Leiber et al. |
| 2012/0037919 A1 | 2/2012 | Xu et al. |
| 2012/0141799 A1* | 6/2012 | Kub .................. B82Y 30/00 428/408 |
| 2012/0325664 A1* | 12/2012 | Shim et al. .................. 204/601 |
| 2013/0037410 A1* | 2/2013 | Xu et al. ..................... 204/601 |
| 2013/0063168 A1 | 3/2013 | Chun |
| 2013/0270521 A1* | 10/2013 | Peng et al. ..................... 257/29 |
| 2015/0028846 A1* | 1/2015 | Zhu ............................. 324/71.5 |

OTHER PUBLICATIONS

He et al., Quantitation of circulating tumor cells in blood samples from ovarian and prostate cancer patients using tumor-specific fluorescent ligands, *Int. J. Cancer*, 123: 1968-1973 (2008).

Venkatesan et al., Stacked Graphene—Al2O3 Nanopore Sensors for Sensitive Detection of DNA and DNA-Protein Complexes, *ACS Nano*, 6(1): 441-450 (2012).

* cited by examiner

NANOPORE DEVICE INCLUDING GRAPHENE NANOPORE AND METHOD OF MANUFACTURING THE SAME

CROSS-REFERENCE TO RELATED APPLICATIONS

This application claims the benefit of Korean Patent Application No. 10-2013-0109974, filed on Sep. 12, 2013, in the Korean Intellectual Property Office, the disclosure of which is incorporated herein in its entirety by reference.

BACKGROUND

1. Field

The present disclosure relates to nanopore devices and methods of manufacturing the same, and more particularly, to nanopore devices with resolution improved by graphene nanopores, and methods of manufacturing the same.

2. Description of the Related Art

Various methods have been developed to detect a target biomolecule, such as a deoxyribonucleic acid (DNA), in a sample. In particular, a nanogap electrode-based method and a nanopore-based method have been proposed as methods for measuring not only the existence and the number of nucleic acids but also a base sequence of each nucleic acid. The nanogap electrode-based method measures a tunneling current in an electrode having a nanogap, and the nanopore-based method measures a current change when a nucleic acid passes through a nanopore that is formed through a thin film.

Recently, a nanopore field effect transistor (FET) device has been widely used. In the nanopore FET device, a nucleic acid is moved toward a nanopore formed through a thin film, such that the nucleic acid passes through the nanopore. For example, when a portion of a nanopore is filled with a sample solution containing a nucleic acid and a voltage is applied across the nanopore, a nucleic acid having a negative charge is moved toward a positive electrode. Therefore, by disposing a negative electrode at the sample solution at one side of the nanopore and disposing the positive electrode on the other side of the nanopore, the nucleic acid may pass through the nanopore.

High resolution may be required to measure a base sequence of the nucleic acid in the nanopore FET device, and the resolution of the nanopore FET device may be determined by the thickness of the nanopore. For example, the resolution of the nanopore FET device may increase as the thickness of the nanopore decreases. In order to measure the base sequence of the nucleic acid, it may be advantageous that the thickness of the nanopore is approximately equal to or smaller than a size of the base interval of the nucleic acid.

SUMMARY

Provided are nanopore devices with resolution improved by graphene nanopores, and methods of manufacturing the same.

Additional aspects will be set forth in part in the description which follows and, in part, will be apparent from the description, or may be learned by practice of the presented embodiments.

According to an example embodiment, a nanopore device includes: a first insulating layer; a graphene layer disposed on the first insulating layer and having a nanopore disposed at a center portion of the graphene layer; and first and second electrode layers disposed respectively at opposite sides of the nanopore on a top surface of the graphene layer, wherein a center region of the first insulating layer has been removed such that the center portion of the graphene layer is.

The nanopore device may further include a second insulating layer disposed on the graphene layer and which covers the first and second electrode layers.

A center region of the second insulating layer may be removed such that the center portion of the graphene layer is exposed to the outside.

The first and second electrode layers may be sealed by the second insulating layer.

The graphene layer may include a multilayer graphene structure having a stack of at least three graphene layers, and a region exposed outside the top graphene layer and the bottom graphene layer among the at least three graphene layers may be passivated to have insulating properties.

The intermediate graphene layer among the at least three graphene layers may have conductivity.

The passivation may combine at least one element of fluorine (F), chlorine (Cl), bromine (Br), and oxygen (O) at exposed surfaces of the top graphene layer and the bottom graphene layer.

The nanopore device may further include a substrate disposed under the first insulating layer, wherein an opening may be formed at a center portion of the substrate to expose the nanopore.

The nanopore device may further include a dielectric layer interposed between the substrate and the first insulating layer, wherein an opening may be formed at a center portion of the dielectric layer to expose the nanopore.

The opening of the substrate may be formed to have a funnel shape such that a width of the opening decreases toward the nanopore.

The nanopore device may further include a first power supply unit configured to generate an electric field between a sample solution, which is disposed on the nanopore, and an electrolyte, which is disposed under the nanopore.

The nanopore device may further include a second power supply unit configured to apply a voltage between the first electrode layer and the second electrode layer.

According to an example embodiment, a method of manufacturing a nanopore device may include: preparing a substrate on a top surface of which a dielectric layer and a first insulating layer are sequentially formed; forming a graphene layer on the first insulating layer; forming first and second electrode layers respectively at both sides on the graphene layer and patterning the graphene layer; exposing a bottom surface of a center region of the first insulating layer and a bottom surface of a center region of the graphene layer by etching a center portion of the substrate; passivating an exposed surface of the graphene layer; and forming a nanopore at an exposed region of the graphene layer.

The forming of the graphene layer may include: partially etching and removing a center portion of the first insulating layer and filling the removed region of the center portion of the first insulating layer, with a selective etch layer; and transferring a graphene layer on the first insulating layer and the selective etch layer.

The forming of the first and second electrode layers and patterning of the graphene layer may include: forming a conductive layer on the graphene layer and patterning the conductive layer; by using the patterned conductive layer as a mask, leaving only the graphene layer under the conductive layer and removing the exposed graphene layer; and removing a center portion of the conductive layer to from divided first and second electrode layers, and exposing a center portion of the graphene layer.

The exposing of the bottom surface of the center region of the first insulating layer and the bottom surface of the center region of the graphene layer may include: removing a center portion of the substrate to form an opening and expose a bottom surface of the dielectric layer formed on the top surface of the substrate; removing an exposed portion of the dielectric layer formed on the top surface of the substrate, to expose the selective etch layer and the bottom surface of the center portion of the first insulating layer; and selectively removing only the selective etch layer to expose the bottom surface of the center region of the graphene layer.

The selective etch layer may be formed of amorphous silicon, and the selective etch layer may be selectively removed by using $XeF_2$ gas.

The passivating of the exposed surface of the graphene layer may be performed by fluorinating the exposed graphene layer by the $XeF_2$ gas when removing the selective etch layer.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
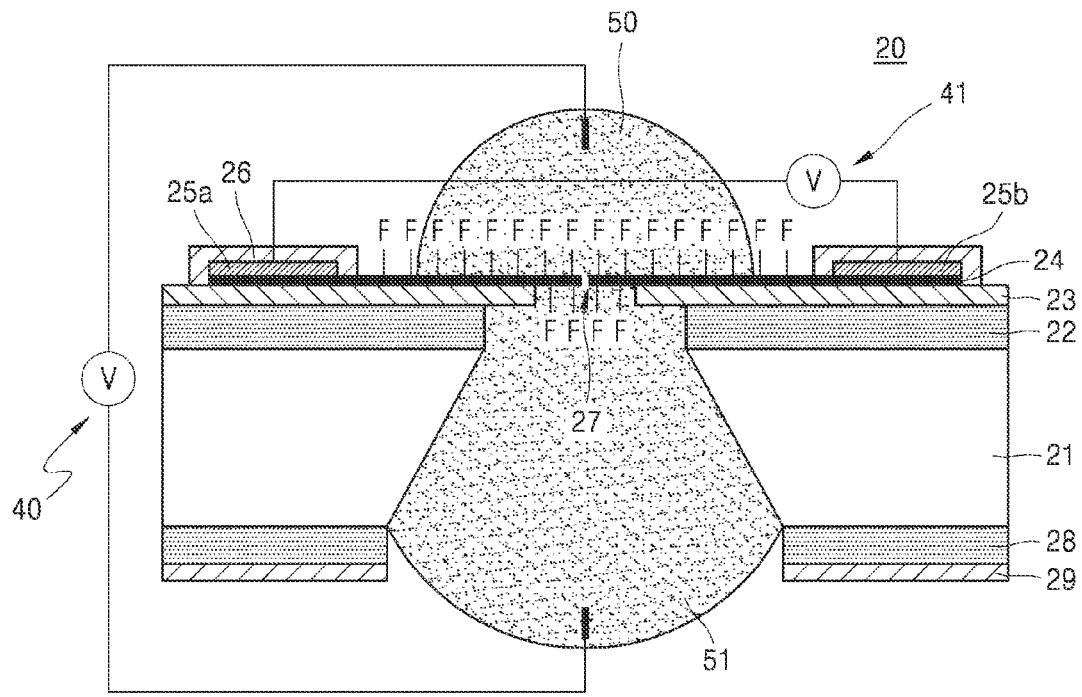
FIG. 1 is a schematic cross-sectional view illustrating a structure of a nanopore device according to an example embodiment.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present description. As used herein, expressions such as "at least one of," when preceding a list of elements, modify the entire list of elements and do not modify the individual elements of the list.

Hereinafter, nanopore devices including graphene nanopores and methods of manufacturing the same will be described in detail with reference to the accompanying drawings. In the drawings, like reference numerals denote like elements, and the thicknesses of layers and regions are exaggerated for clarity. The embodiments described hereinafter are merely exemplary, and various changes and modifications may be made therein. It will be understood that when a layer is referred to as being "on" another layer or substrate, it may be directly on the other layer or substrate, or one or more intervening layers may also be present.

FIG. 1 is a schematic cross-sectional view illustrating a structure of a nanopore device according to an example embodiment.

Referring to FIG. 1, a nanopore device 20 according to the present embodiment may include a first insulating layer 23, a graphene layer 24 disposed on the first insulating layer 23 and having a nanopore 27 formed at a center portion thereof, first and second electrode layers 25a and 25b disposed respectively at both sides of the nanopore 27 on a top surface of the graphene layer 24, and a second insulating layer 26 formed on the graphene layer 24 so as to cover the first and second electrode layers 25a and 25b.

For example, the first insulating layer 23 may be formed of $SiO_2$, or $SiN_x$, $Al_2O_3$. The first and second electrode layers 25a and 25b may be formed of a conductive material such as a metal. For example, the first and second electrode layers 25a and 25b may be formed of gold (Au) or titanium (Ti). Also, the first and second electrode layers 25a and 25b may be formed to have a dual-layer structure of Ti/Au. The second insulating layer 26 prevents the first and second electrode layers 25a and 25b from contacting a sample solution 50 which would generate a leakage current. For example, the second insulating layer 26 may be formed of $Al_2O_3$ or polymer-based material. However, when the first and second electrode layers 25a and 25b do not contact the sample solution 50, the second insulating layer 26 may be omitted. The first insulating layer 23 and the second insulating layer 26 may have a thickness of about 30 nm.

According to the present embodiment, since center portions of the first insulating layer 23 and the second insulating layer 26 are removed, a center portion of the graphene layer 24 is exposed, e.g., exposed to the outside or external environment. The nanopore 27 may be formed at the center portion of the graphene layer 24 that is exposed to the outside. Other regions on the top and bottom of the graphene layer 24, other than the center portions of the graphene layer 24, may be sealed by the first insulating layer 23 and the second insulating layer 26.

For example, by irradiating a focused electron beam by a transmission electron microscope (TEM) equipment, the nanopore 27 may be formed through the graphene layer 24. The nanopore 27 may be formed to have a diameter of about 10 nm or less, for example, about 2 nm or less. Since the center portions of the first insulating layer 23 and the second insulating layer 26 are removed, the thickness of the nanopore 27 may depend only on the thickness of the graphene layer 24. For example, the nanopore 27 may have a thickness of about 1 nm. Therefore, according to the present embodiment, the nanopore device 20 of a field effect transistor (FET) type having the nanopore 27 with a relatively small thickness may be provided.

Figure 2:
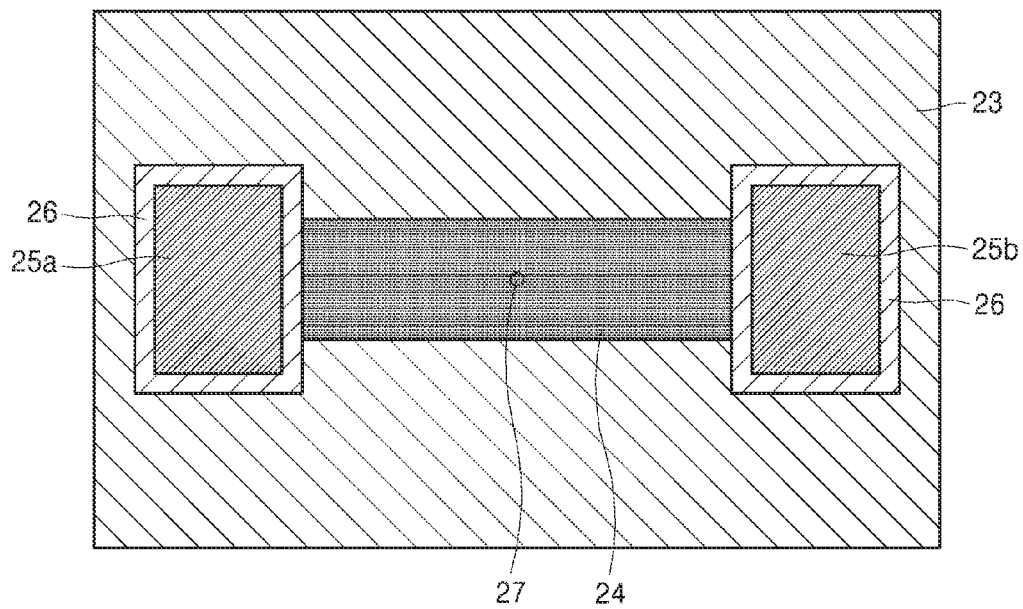
FIG. 2 is a schematic plan view illustrating a disposition relation between a first insulating layer, a graphene layer, electrode layers, and a second insulating layer illustrated in FIG. 1.

FIG. 2 is a schematic plan view illustrating a disposition relation between the first insulating layer 23, the graphene layer 24, the first and second electrode layers 25a and 25b, and the second insulating layer 26 illustrated in FIG. 1. Referring to FIG. 2, the graphene layer 24, elongated in one direction, is disposed on the first insulating layer 23, and the first and second electrode layers 25a and 25b are disposed respectively at both ends of the elongated graphene layer 24. Also, the second insulating layer 26 is formed at both ends of the graphene layer 24 to cover the first and second electrode layers 25a and 25b. The nanopore 27 may be formed at the center portion of the graphene layer 24 that is exposed between the second insulating layers 26.

Referring to FIG. 1, the nanopore device 20 may further include a substrate 21 having an opening that passes through a center portion thereof. For example, the substrate 21 may be formed of silicon (Si). The first insulating layer 23 may be disposed on a top side of the substrate 21, and the nanopore 27 may be exposed through the opening formed at the center portion of the substrate 21. The opening may be formed to have a funnel shape such that a width thereof decreases toward the nanopore 27. Also, in order to prevent the leakage of an electrolyte 51 and a current, a dielectric layer 22 may be additionally disposed between the substrate 21 and the first insulating layer 23, and a dielectric layer 28 and an insulating layer 29 may be additionally disposed under, or on the bottom side of, the substrate 21. For example, the dielectric layer 22 may be formed of $SiO_2$ and may have a thickness of about 100 nm to about 300 nm. Also, an opening may be formed at a center portion of the dielectric layer 22 to expose the nanopore 27.

On the exposed graphene layer 24 of the nanopore device 20, the sample solution 50 containing a target biomolecule, such as a nucleic acid, may be disposed to cover the nanopore 27. For the convenience of description, the size of the sample solution 50 is exaggerated in FIG. 1. However, an actual sample solution 50 may be formed in the shape of a droplet on the nanopore device 20. The electrolyte 51, through which a current may flow, may be received in the opening of the substrate 21 under the first insulating layer 23. The electrolyte 51 may be the same solution as the sample solution 50. For example, the electrolyte 51 may be a conductive solution such as a KCL solution. That is, the sample solution 50 may be disposed on the nanopore 27, and the electrolyte 51 may be disposed under the nanopore 27.

The nanopore device 20 may further include a power supply unit 40 configured to generate an electric field in the sample solution 50 and the electrolyte 51 to cause the target biomolecules of the sample solution 50 to pass through the nanopore 27 and move to the electrolyte 51. In certain aspects, the power supply unit 40 may include two electrodes that are immersed respectively in the sample solution 50 and the electrolyte 51. Also, the nanopore device 20 may further include an additional power supply unit 41 configured to apply a voltage between the first electrode layer 25a and the second electrode layer 25b. In this structure, nucleic acids may be detected by measuring a voltage change that occurs between the two electrodes of the power supply unit 40 immersed respectively in the sample solution 50 and the electrolyte 51, when the target biomolecules pass through the nanopore 27.

For example, when a predetermined voltage is applied to the sample solution 50 and the electrolyte 51 by the power supply unit 50, the nucleic acids in the sample solution 50 moves along the electric field generated between the sample solution 50 and the electrolyte 51. For example, when a voltage of 0V is applied to the sample solution 50 and a positive (+) voltage is applied to the electrolyte 51, each of the nucleic acids of the sample solution 50 may pass through the nanopore 27 and move to the electrolyte 51. While the nucleic acids pass through the nanopore 27, a voltage change occurs around the nanopore 27. Since most of the voltage between the two electrodes of the power supply unit 40 immersed respectively in the sample solution 50 and the electrolyte 51 is concentrated around the nanopore 27, the voltage change around the nanopore 27 is substantially equal to the voltage change between the two electrodes of the power supply unit 40. Thus, nucleic acids may be detected by detecting a voltage change between the two electrodes of the power supply unit 40 immersed respectively in the sample solution 50 and the electrolyte 51. The voltage change between the two electrodes of the power supply unit 40 may be detected from a change in the current flowing along the graphene layer 24. For example, the voltage change between the two electrodes of the power supply unit 40 may be detected by measuring a current change occurring between the first electrode layer 25a and the second electrode layer 25b on the graphene layer 24. In this case, the sensitivity of the nanopore device 20 may be controlled by controlling the voltage between the first electrode layer 25a and the second electrode layer 25b.

In the present embodiment, in order to prevent a current leakage from occurring through the center portion of the graphene layer 24 that is exposed, the graphene layer 24 may include a multilayer graphene structure having a stack of at least three or more layers. For example, referring to FIG. 3, the graphene layer 24 may include three graphene layers 24a, 24b and 24c. Among the graphene layers 24a, 24b and 24c, the top graphene layer 24b and the bottom graphene layer 24c function as a passivation layer for preventing a current leakage. In certain aspects, by surface-treating the exposed regions of the top graphene layer 24b and the bottom graphene layer 24c, elements such as fluorine (F), chlorine (Cl), bromine (Br), or oxygen (O) may be combined at the exposed surfaces of the top graphene layer 24b and the bottom graphene layer 24c. The top graphene layer 24b and the bottom graphene layer 24c, which are surface-passivated, lose original electrical characteristics (conductivity) and have insulating properties. On the other hand, the intermediate graphene layer 24a maintains original electrical characteristics (high conductivity), and may be electrically insulated from the outside by the top and bottom graphene layers 24b and 24c.

Figure 3:
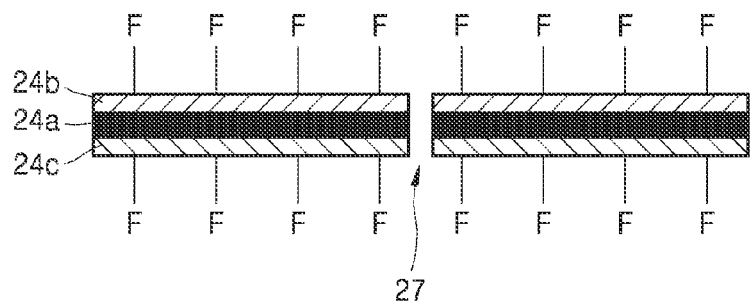
FIG. 3 is a schematic diagram illustrating a plurality of graphene layer portions at which nanopores are formed in the nanopore device illustrated in FIG. 1.

Therefore, when the nucleic acids pass through the nanopore 27, a current change may be measured by the intermediate graphene layer 24a, and a current leakage may be prevented by the top graphene layer 24b and the bottom graphene layer 24c that are surface-treated. Only three graphene layers 24a, 24b and 24c are illustrated in FIG. 3; however, more surface-treated graphene layers may be used to obtain sufficient passivation effects. For example, the graphene layer 24 may include a multilayer graphene structure having a stack of ten or more layers.

As described above, in the nanopore device 20 according to the present embodiment, the thickness of the nanopore 27 depends only on the thickness of the graphene layer 24. For example, since one layer of graphene has a thickness of about 0.34 nm, when the graphene layer 24 is formed to have a stack of three graphenes, the graphene layer 24 may have a thickness of about 1 nm. That is, the nanopore 27 has a thickness of only about 1 nm. Therefore, since the nanopore device 20 illustrated in FIG. 1 may have the nanopore 27 with a very small thickness, the base sequence of the nucleic acid may be analyzed very accurately at high resolution.

FIGS. 4A to 4L are cross-sectional views illustrating a process of manufacturing the nanopore device 20 illustrated in FIG. 1.

Figure 4A:
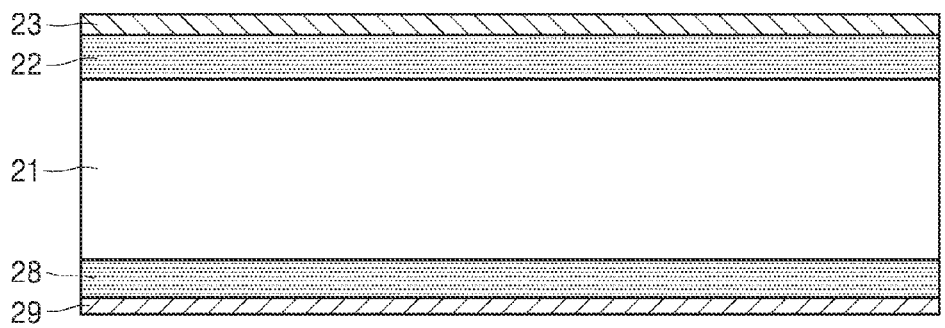
FIGS. 4A to 4L are cross-sectional views illustrating a process of manufacturing the nanopore device illustrated in FIG. 1.

Referring to FIG. 4A, a substrate 21, which has a top surface and a bottom surface on which dielectric layers 22 and 28 and insulating layers 23 and 29 are symmetrically stacked, is provided. For example, the substrate 21 may be a silicon substrate. For example, the dielectric layers 22 and 28 may be formed of $SiO_2$ and may have a thickness of about 100 nm to about 300 nm. For example, the insulating layers 23 and 29 may be formed of $SiO_2$, $SiN_x$, or $Al_2O_3$ and may have a thickness of about 30 nm. The dielectric layer 28 and the insulating layer 29 disposed under the substrate 21 are used as a mask for forming an opening at the substrate 21, and may be removed afterwards. Also, when the leakage of an electrolyte and a current may be sufficiently prevented solely by the first insulating layer 23, the dielectric layer 22 disposed on the substrate 21 may be omitted.

Figure 4B:
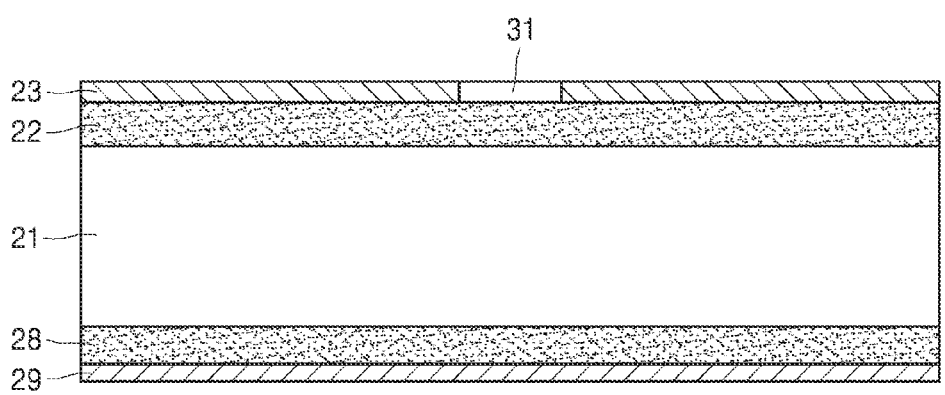

Referring to FIG. 4B, a center portion of the first insulating layer 23 is partially etched and removed, and the removed region resulting from the etching of the first insulating layer 23 is filled with a selective etch layer 31. For example, the selective etch layer 31 may be formed of amorphous silicon (a-Si) or a metal material. The selective etch layer 31 may have a width of about 1 μm or less. For example, the selective etch layer 31 may have a width of about 100 nm to about 1 μm, or a width of about 100 nm or less. However, the width of the selective etch layer 31 may be greater than 1 μm as long as it is smaller than the width of a graphene layer 24 to be formed later.

Figure 4C:
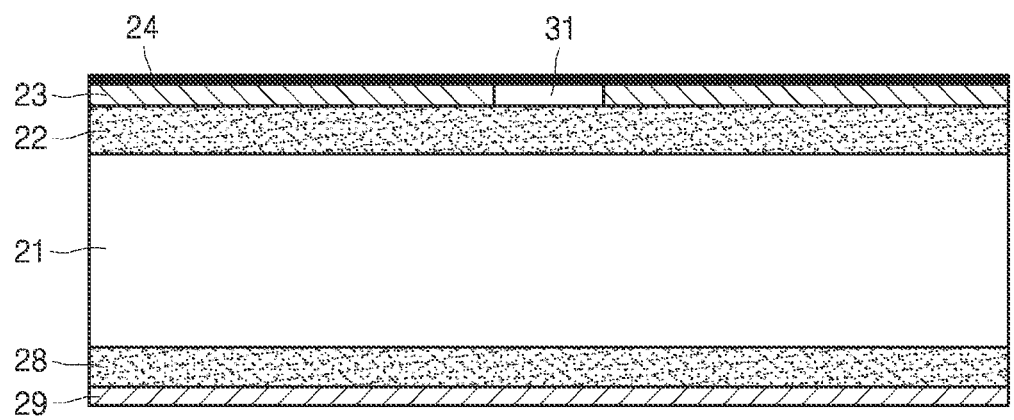

Referring to FIG. 4C, a graphene layer 24 is transferred completely onto the first insulating layer 23 and the selective etch layer 31. As described above, the graphene layer 24 may include a multilayer graphene structure having a stack of three or more layers. The graphene layer 24 may be formed by sequentially stacking separate single graphene layers, or by transferring a preformed graphene layer having the multilayer structure onto the first insulating layer 23 and the selective etch layer 31.

Figure 4D:
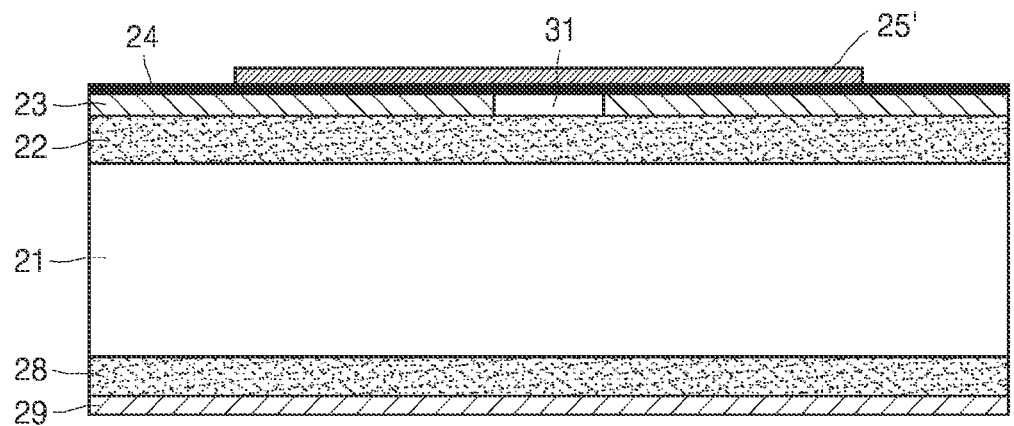

Referring to FIG. 4D, a conductive layer 25' is formed on the graphene layer 24, and an edge of the conductive layer 25' is removed and patterned. Accordingly, the conductive layer 25' is left on a center portion of the graphene layer 24, and both edges of the graphene layer 24 are exposed. For example, the conductive layer 25' may be formed of a high-conductivity metal material such as gold (Au) or titanium (Ti).

Figure 4E:
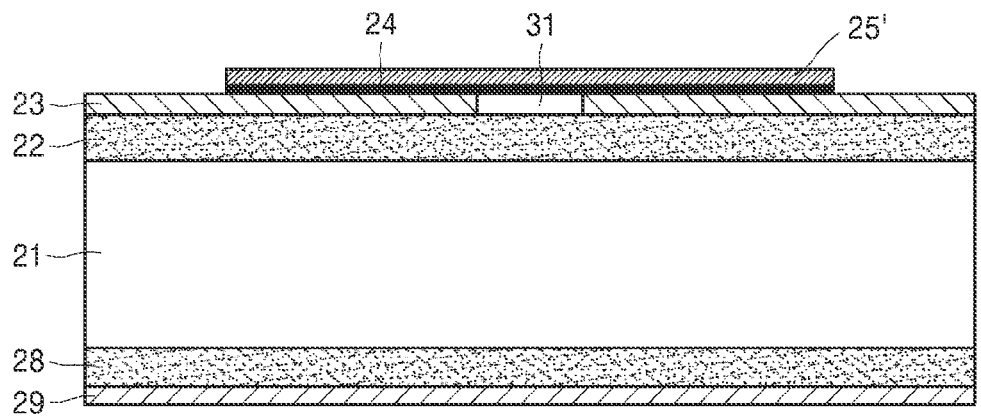
Figure 4F:
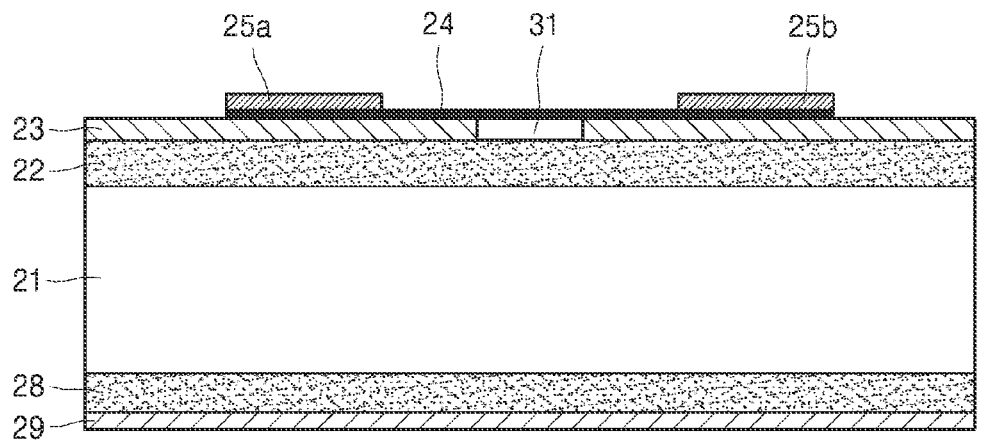

Referring to FIG. 4E, using the conductive layer 25' as a hard mask, only the center portion of the graphene layer 24 is left and the exposed portion of the graphene layer 24 is etched and removed. Accordingly, only the graphene layer 24 under the conductive layer 25' is left, the exposed portion of the graphene layer 24 around the conductive layer 25' is removed, and both edges of the first insulating layer 23 are partially exposed. Referring to FIG. 4F, a center portion of the conductive layer 25' is etched and removed. Then, the conductive layer 25' is divided into two parts, and the two parts of the conductive layers 25' become first and second electrode layers 25a and 25b respectively. Also, a portion of the graphene layer 24 located between the first electrode layer 25a and the second electrode layer 25b is exposed.

Figure 4G:
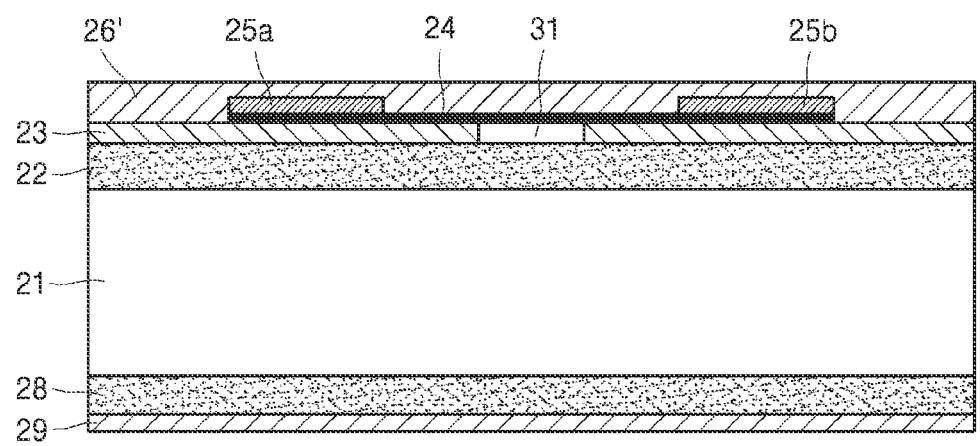
Figure 4H:
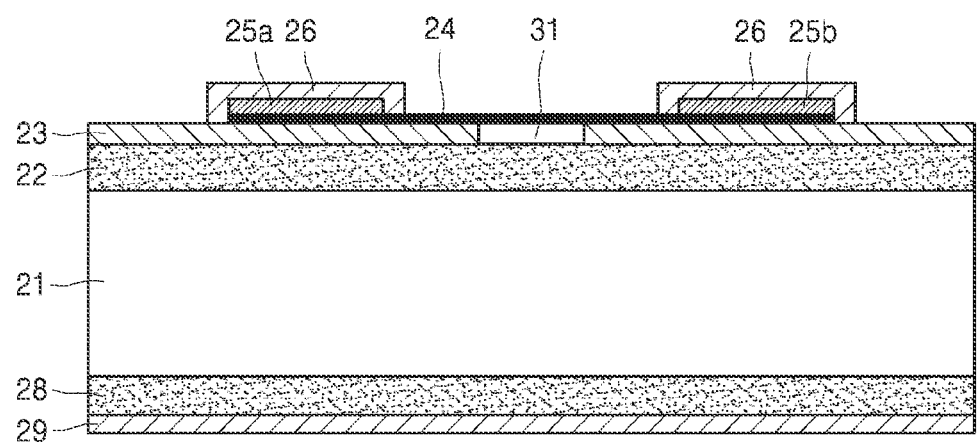

Referring to FIG. 4G, an insulating material layer 26' is deposited to completely cover the first and second electrode layers 25a and 25b, the exposed portion of the graphene layer 24, and the exposed portion of the first insulating layer 23. For example, the insulating material layer 26' may be formed of $Al_2O_3$ or a polymer-based material. Referring to FIG. 4H, the insulating material layer 26' is patterned to form a second insulating layer 26 that passivates the first and second electrode layers 25a and 25b. The second insulating layer 26 may completely cover and seal the first and second electrode layers 25a and 25b, thereby preventing a current leakage. In this case, both edges of the first insulating layer 23 and the center portion of the graphene layer 24 are exposed again.

Figure 4I:
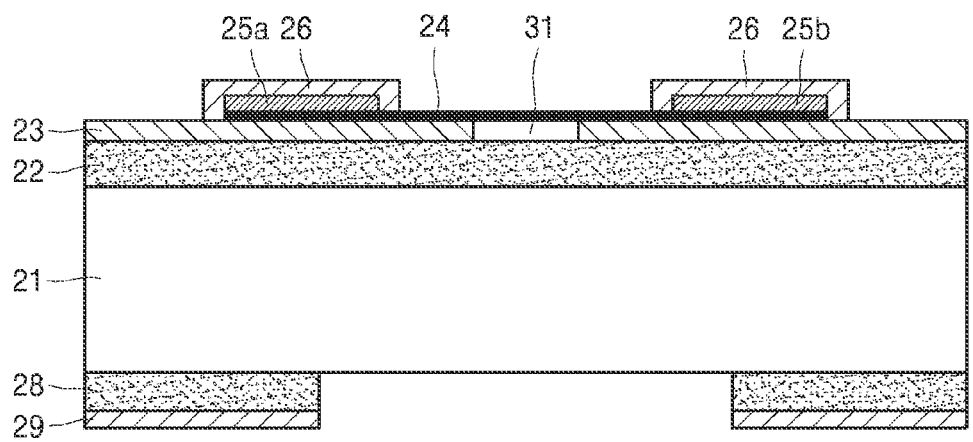
Figure 4J:
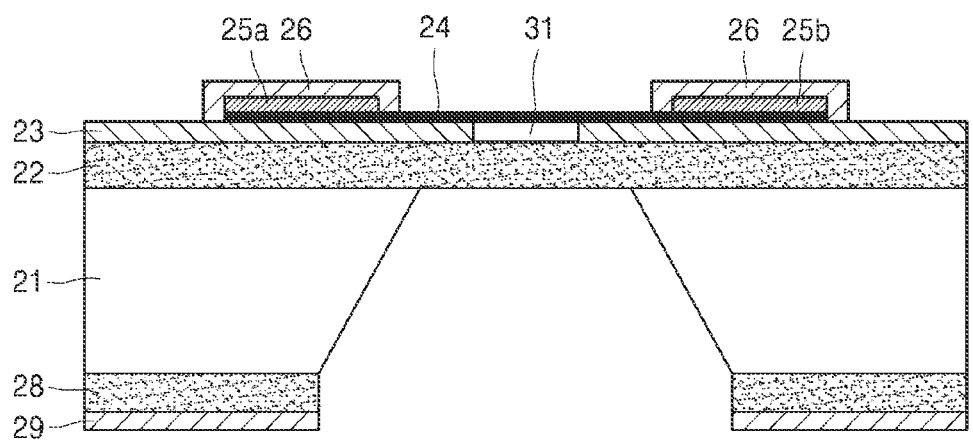
Figure 4K:
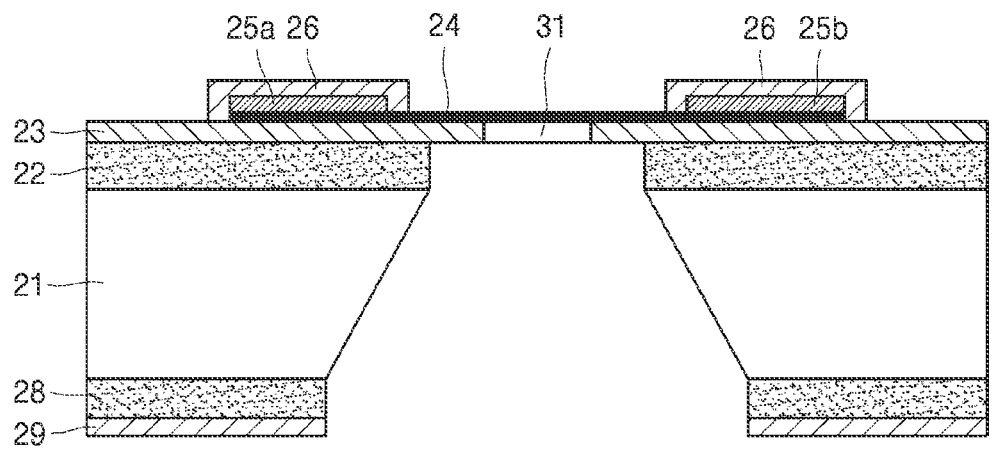

Referring to FIG. 4I, the center portions of the dielectric layer 28 and the insulating layer 29 located under the substrate 21 are etched and removed. Then, the center portion of the substrate 21 is partially exposed. As illustrated in FIG. 4I, the width of the exposed portion of the substrate 21 may be larger than the width of the exposed portion of the graphene layer 24. Referring to FIG. 4J, using the remaining dielectric layer 28 and insulating layer 29 as a mask, the exposed portion of the substrate 21 is etched and removed. Accordingly, a funnel-shaped opening may be formed at the center portion of the substrate 21, and the bottom surface of the center portion of the dielectric layer 22 is exposed. Referring to FIG. 4K, the exposed portion of the dielectric layer 22 is etched and removed. Accordingly, the bottom surface of the center portion of the first insulating layer 23 and the selective etch layer 31 may be exposed.

Figure 4L:
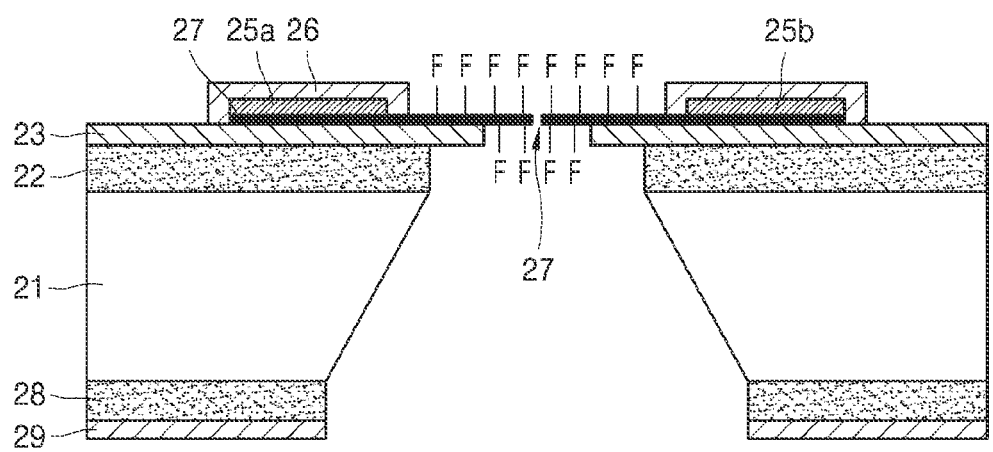

Referring to FIG. 4L, the selective etch layer 31 is completely etched and removed. For example, when the selective etch layer 31 is formed of amorphous silicon (a-Si), the selective etch layer 31 may be selectively removed by $XeF_2$ gas. In this case, both the top surface and the bottom surface of the center portion of the graphene layer 24 may be exposed. Depending on the width of the selective etch layer 31, as illustrated in FIG. 4L, the width of the exposed top surface of the graphene layer 24 may be larger than the width of the exposed bottom surface of the graphene layer 24. Also, since the exposed region of the graphene layer 24 is fluorinated by $XeF_2$ gas when removing the selective etch layer 31, the exposed graphene layers 24b and 24c may form a passivation layer as illustrated in FIG. 4L. Finally, when a nanopore 27 is formed at the graphene layer 24 through a TEM process, the nanopore device 20 may be completed.

As described above, according to the one or more of the above embodiments, since the nanopore device 20 has the nanopore 27 formed using graphene, the resolution thereof may be improved by reducing the thickness of the nanopore 27. Also, the nanopore device 20 may include the graphene layer 24 having a stack of at least three layers, and the intermediate graphene layer may be insulated from the outside by forming a chemical passivation at the top and bottom layers of the graphene layer 24. Therefore, since it is not necessary to use a separate thick insulating layer, the nanopore 27 may be formed to be thinner.

It should be understood that the exemplary embodiments described therein should be considered in a descriptive sense only and not for purposes of limitation. Descriptions of features or aspects within each embodiment should typically be considered as available for other similar features or aspects in other embodiments.

While one or more embodiments have been described with reference to the figures, it will be understood by those of ordinary skill in the art that various changes in form and details may be made therein without departing from the spirit and scope of the present invention as defined by the following claims.

What is claimed is:

1. A nanopore device comprising:
   a first insulating layer;
   a multilayer graphene structure disposed on the first insulating layer and having a nanopore disposed at a center portion of the multilayer graphene structure; and
   first and second electrode layers disposed respectively at opposite sides of the nanopore on a top surface of the multilayer graphene structure,
   wherein a center region of the first insulating layer has been removed such that the center portion of the multilayer graphene structure is exposed,
   wherein the multilayer graphene structure comprises:
   a bottom graphene layer disposed on the first insulating layer;
   an intermediate graphene layer directly disposed on the bottom graphene layer; and
   a top graphene layer directly disposed on the intermediate graphene layer, a center portion of an upper surface of the top graphene layer being exposed, wherein each of the bottom, intermediate and top graphene layers is formed of graphene,
wherein a width of the removed center region of the first insulating layer is larger than a diameter of the nanopore such that a center portion of a lower surface of the bottom graphene layer is exposed.

2. The nanopore device of claim 1, further comprising a second insulating layer disposed on the multilayer graphene structure and which covers entire side surfaces and entire top surfaces of the first and second electrode layers such that the first and second electrode layers are sealed between the second insulating layer and the multilayer graphene structure, thereby preventing a current leakage.

3. The nanopore device of claim 2, wherein a center region of the second insulating layer is removed such that the center portion of the multilayer graphene structure is exposed.

4. The nanopore device of claim 1, wherein an exposed region of the top graphene layer and the bottom graphene layer is passivated to have insulating properties.

5. The nanopore device of claim 4, wherein the passivated exposed region of the top graphene layer and the bottom graphene layer combines at least one element of fluorine (F), chlorine (Cl), and bromine (Br) at exposed surfaces of the top graphene layer and the bottom graphene layer.

6. The nanopore device of claim 1, wherein the intermediate graphene layer is conductive.

7. The nanopore device of claim 1, further comprising a substrate disposed under the first insulating layer,
wherein an opening is disposed at a center portion of the substrate so as to expose the nanopore.

8. The nanopore device of claim 7, further comprising a dielectric layer interposed between the substrate and the first insulating layer,
wherein an opening is disposed at a center portion of the dielectric layer so as to expose the nanopore.

9. The nanopore device of claim 7, wherein the opening of the substrate has a funnel shape wherein a width of the opening decreases toward the nanopore.

10. The nanopore device of claim 1, further comprising:
a first power supply unit configured to generate an electric field between a sample solution, which is disposed on the nanopore, and an electrolyte, which is disposed under the nanopore; and
a second power supply unit configured to apply a voltage between the first electrode layer and the second electrode layer.

11. The nanopore device of claim 1, wherein the multilayer graphene structure has a thickness of about 1 nm.

12. The nanopore device of claim 1, wherein lengths of the bottom, intermediate and top graphene layers are identical to each other.

* * * * *